US00PP17336P2

(12) United States Plant Patent
Decourtye

(10) Patent No.: US PP17,336 P2
(45) Date of Patent: Jan. 2, 2007

(54) ***PACHYSTEGIA* PLANT NAMED 'HARDEC'**

(50) Latin Name: *Pachystegia insignis*
Varietal Denomination: Hardec

(75) Inventor: M. Luc Decourtye, Molitg les Bains (FR)

(73) Assignee: Agri-Obtentions S.A., Guyancourt Cedex (FR)

( * ) Notice: Subject to any disclaimer, the term of this patent is extended or adjusted under 35 U.S.C. 154(b) by 30 days.

(21) Appl. No.: 11/154,656

(22) Filed: Jun. 17, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

Agri Obtentions [online], [retrieved on Mar. 30, 2006]. Retrieved from the Internet <http://www.agri–obtention-s.fr/> one page.*
UPOV–ROM GTITM Plant Variety Database, 2005/05, GTI Jouve Retrieval Software, Citation for *Pachystegia* 'Hardec'.*

* cited by examiner

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct *Pachystegia insignis* plant is provided that displays in profusion attractive sterile composite flowers having pure white ray florets and yellow disc florets. The overall growth habit is bushy. Dense greyed-green foliage is formed. The new cultivar is well suited for providing attractive ornamentation in the gardens where the climate is moderate. Alternatively, the cultivar can be grown in pots or other containers indoors.

2 Drawing Sheets

Botanical/commercial classification: *Pachystegia insignis/Pachystegia* Plant.
Varietal denomination: cv. Hardec.

SUMMARY OF THE INVENTION

A new and distinct cultivar of *Pachystegia* plant is provided that is botanically known as *Pachystegia insignis.*

The new cultivar was the product of a breeding program carried out at Angers, France, during 1986. The parents of the new cultivar were progeny of plants introduced from New Zealand, and a fuller identification of the parents is not available. Accordingly, the parent plants of the new cultivar are unknown. The plant of the new cultivar was selected during 1986 at Angers, France.

It was found that a single plant from the breeding program displayed the following combination of characteristics:

(a) displays a profusion of attractive sterile composite flowers having pure white ray florets and yellow disc florets, (b) displays a bushy growth habit, (c) forms dense greyed-green foliage, and (d) is well suited for providing attractive ornamentation when grown in gardens and in containers indoors.

The attractive blossoms of the new cultivar are well borne over the entire plant. The new cultivar well meets the needs of horticultural industry. It can be grown to advantage in the landscape where the climate is moderate, and in pots or other containers. Temperatures as low as −5° C. have been tolerated. When grown at Angers, France, the new cultivar has been sterile during observations to date.

The new cultivar of the present invention can be readily distinguished from the 'Minor' cultivar (non-patented in the United States) of *Pachystegia insignis.* More specifically, the parts of the 'Minor' cultivar are believed to be smaller and more slender. No other recognized cultivars of *Pachystegia insignis* are known for comparison.

The new cultivar has been asexually reproduced at Angers, France, by *in vitro* culture. The characteristics of the new cultivar are firmly fixed and the new cultivar has been demonstrated to reproduce in a true to type manner in subsequence generations.

The new cultivar has been named 'Hardec'.

BRIEF DESCRIPTION OF THE PHOTOGRAPH

The accompanying photographs show plants having an age of approximately 2½ years during the summer when grown at Angers, France.

DETAILED DESCRIPTION

Figure 1:
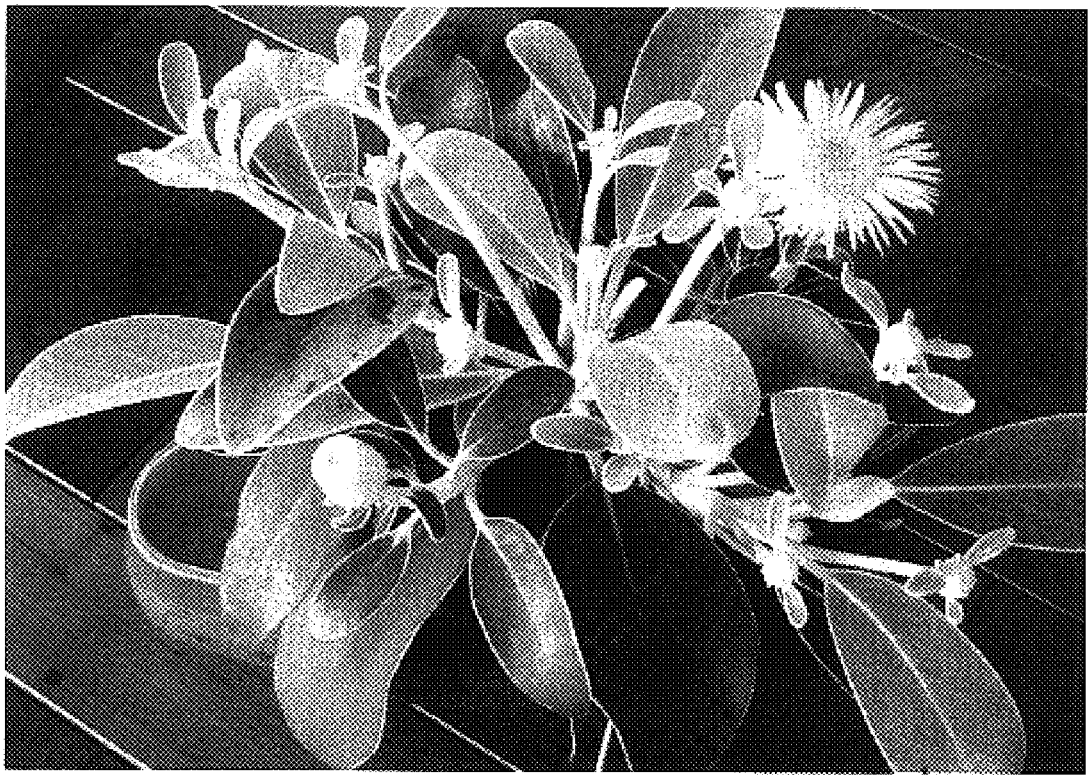
FIG. 1 shows the overall appearance of a flowering plant.
Figure 2:
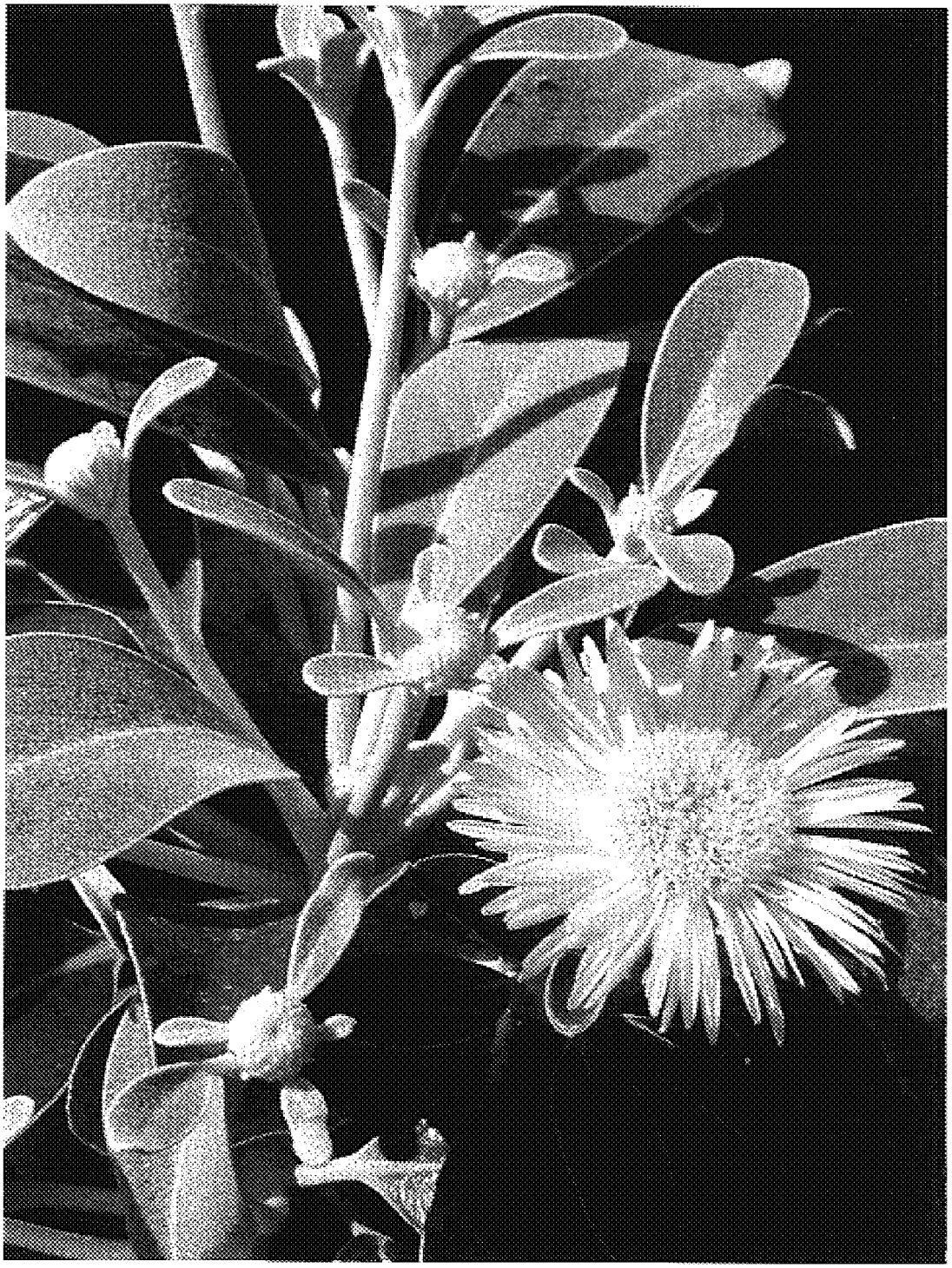
FIG. 2 shows a closer view of a fully-opened inflorescence wherein the pure white ray florets and yellow disc florets appear, buds in various stages of development, and the attractive greyed-green foliage.

The following description is based on the observation of four year-old plants of the new cultivar growing in pots during June 2005, at Angers, France. Such plants had been asexually reproduced through the use of tissue culture. Reference to The R.H.S. Colour Chart of The Royal Horticultural Society, London, England, is provided. Common color terms are accorded their customary dictionary significance.

Origin: A product of a controlled breeding program through the use of unknown parents.

Plant:

*Habit.*—Bushy.

*Height.*—Approximately 60 cm on average.

*Width.*—Approximately 90 cm on average.

*General appearance.*—Half woody with compact bunches of leaves.

Branches:

*Color.*—Greyed-Green Group 195C for young stems, and Greyed-Brown Group 199D on adult stems.

*Configuration.*—Substantially round in cross section.

*Internode length.*—Approximately 20 cm on average.

*Texture.*—Smooth and very slightly pubescent.

Foliage:

*General appearance.*—Dense and greyed-green in coloration.

*Configuration.*—Obovate.

*Margin.*—Entire.

*Base.*—Obtuse.

*Apex.*—Obtuse.

*Texure.*—Young leaves are densely tomentose, and mature leaves are glossy on the upper surface with a thin edge of tomentum.

*Length.*—Approximately 11 to 18 cm on average.

*Width.*—Approximately 6 to 10 cm on average.

*Number of leaves per stem.*—Commonly approximately 10 on average.

*Color.*—Upper surface: near Greyed-Green Group 195C for young foliage, and near Yellow-Green Group 147A for adult foliage. Under surface: near Greyed-Green Group 195C for young foliage, and for adult foliage.

*Petiole.*—Rigid, pubescent in texture, approximately 6 cm in length on average, and near Greyed-Green Group 195C in coloration.

Inflorescence:

*External sepals.*—Closely aligned, pubescent in texture, and near White Group 155D in coloration on the outer surface.

*Calyx.*—Approximately 2.5 cm in length, and near White Group 155C in coloration.

*Peduncle.*—Pubescent in texture, approximately 35 cm in length on average, approximately 0.6 cm in diameter on average, and near Greyed-Green Group 195C in coloration.

*Time of blooming.*—Commonly from the end of May to the end of June.

*Duration of blooming.*—Approximately one month depending upon the average temperature.

*Buds.*—Initially globose, becoming oblong, approximately 2.1 to 2.9 cm in length on average, and approximately 1.7 in width on average.

*Size.*—A fully open flower commonly measures approximately 5 cm in diameter.

*Ray florets.*—Approximately 84 in number on average, acute and fused towards the base, rounded apex, approximately 3 cm in length on average including the fused portion, and pure white, White Group 155B, in coloration.

*Disc florets.*—Approximately 300 in number on average, approximately 1.8 cm in length on average, approximately 0.1 cm in width on average, and near Yellow Group 13A in coloration.

*Filaments.*—Five in number, present with disc florets, fused at the upper part, approximately 0.5 cm in size on average, and near White Group 155B in coloration.

*Pollen.*—Near Greyed-Green Group 195C in coloration.

*Styles.*—Present with disc and ray florets, approximately 2.2 cm in size, and near White Group 155B in coloration.

*Stigma.*—Bilobed when mature, approximately 0.5 cm in size, and near White Group 155B in coloration.

*Hips.*—None observed with the plants being fully sterile during observations to date at Angers, France.

*Lastingness of a flower.*—Commonly approximately 3 weeks on average depending upon the environmental conditions.

No particular susceptibility to plant diseases has been noted for the species in Europe during observations to date.

Plants of the new 'Hardec' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Pachystegia* plant characterized by the following characteristics:

(a) displays a profusion of attractive sterile composite flowers having pure white ray florets and yellow disc florets, (b) displays a bushy growth habit, (c) forms dense greyed-green foliage, and (d) is well suited for providing attractive ornamentation when grown in gardens and in containers indoors;

substantially as illustrated and described.

* * * * *